United States Patent [19]

Schwartz

[11] Plant 4,264

[45] June 13, 1978

[54] ROSE PLANT

[75] Inventor: Ernest Schwartz, Kingsville, Md.

[73] Assignee: F. Harmon Saville, Rowley, Mass.

[21] Appl. No.: 821,818

[22] Filed: Aug. 4, 1977

[51] Int. Cl.[2] ..... A01H 5/00

[52] U.S. Cl. ..... Plt./9

[58] Field of Search ..... Plt./9

*Primary Examiner*—Robert E. Bagwill

*Assistant Examiner*—James R. Feyrer

*Attorney, Agent, or Firm*—Vincent G. Gioia

[57] ABSTRACT

A pink miniature rose plant, resulting from "Ma Perkins" × "Baby Betsy McCall", which has a high centered, recurrent flowering habit. Light lavender pink toned flowers are borne primarily singly on long straight stems.

1 Drawing Figure

1

The present invention relates to a new and distinct variety of rose plant of the miniature rose class, which was originated by my crossing as seed parent the floribunda rose known as "Ma Perkins" and the miniature rose known as "Baby Betsy McCall" as pollen parent.

Among the novel characteristics possessed by this new variety which distinguish it from its parents and all other varieties of which I am aware are: (1) recurrent blooms with petals creasing to produce a spiral, circular outline presenting a symmetrical aspect, (2) high centered flowers borne primarily singly on long cutting stems, (3) flower coloring deeper at the underside of petals than the top side presenting a "two-tone" effect as the flower opens, and (4) very floriferous plants. Asexual reproduction by budding of the new variety as performed in Essex County, Mass., shows that the foregoing and other distinguishing characteristics come true to form and are established and transmitted through succeeding propagations.

The new and improved rose variety which I have developed is a fine miniature rose of unusual coloring due to deeper coloring of the undersides of the petals than the top sides. This difference in hue produces an attractive "two-tone" effect upon opening which is especially appealing because of the physical structure of the flowers. The petals reflex and crease so as to produce a spiral, circular outline. Since the plant is quite floriferous, there is an eye-catching lavender-pink tonality when viewed at a distance. Another outstanding feature is that the hybrid-tea shaped blooms are borne singly on long cutting stems. The flowers are unusually heavily petaled, for a miniature rose with as many as 45 to 50 having been counted. Despite this heavy petalage, the blooms open well and hold their unusual coloring.

The accompanying drawing shows typical specimens of the vegetative growth and flowers of the new variety in different stages of development and as depicted in color as nearly true as it is reasonably possible to make the same in color illustration of this character.

The following is a detailed description of my new variety, with color terminology in accordance with the Royal Horticultural Society Color Chart (RHSCC). The terminology used in color description herein refers to plate numbers in the aforementioned color chart, e.g., "52B" is plate 52B of the Royal Horticultural Society Color Chart.

Parentage:

*Seed parent.*—"Ma Perkins."

2

*Pollen parent.*—"Baby Betsy McCall."

Class: Miniature.

The following observations are made of specimens grown in a greenhouse at Essex County, Mass. during the month of May.

FLOWER

Blooming habit: Continuous.

Bud:

*Size.*—Medium.

*Form.*—Pointed.

*Color.*—When sepals first divide — 55A. When petals begin to unfurl — 55B. When half-blown: 55B. Reverse side of petals — 54A.

*Sepals.*—Smooth, pointed, shorter than the opening bud.

*Peduncle.*—Length — $1\frac{1}{4}$ to $1\frac{3}{4}$ inches. Aspect — straight. Strength — erect. Color — 145A.

Bloom:

*Size.*—Average size when fully expanded-about $1\frac{1}{2}$ inches.

*Borne.*—Primarily singly, occasionally three to a stem (2 side buds).

*Form.*—High centered blooms at first becoming flat when fully opened, petals crease longitudinally and produce a spiral, circular outline, very symmetrical.

*Petalage.*—Number of petals under normal conditions — about 45 to 50.

*Color (during first 2 days).*—Inner petals at center of flower — 52B. Outer petals — 55C. Base of petals (point of attachment) — 2C. Reverse of petals — 55B. General tonality from a distance — lavender pink.

*Color change.*—As bloom ages — outer petals lighten and color of inner petals becomes deeper and after several days the general tonality lightens to near 56C.

Petals:

*Texture.*—Medium.

*Appearance.*—Satiny inside and outside.

*Form.*—Rounded, nearly circular.

*Arrangement.*—Regularly arranged, shingle-like, imbricated.

*Petaloids in center.*—Few.

*Persistence.*—Drop off cleanly.

*Fragrance.*—Moderate to strong, sweet.

*Lasting quality.*—Very good on plant and as cut flower.

REPRODUCTIVE ORGANS

Stamens, filaments and anthers:

*Arrangement.*—Few intermixed with petaloids.

*Color.*—13C.

Pollen: Little or none.

Styles: Uneven, thin, occasionally vegetative.

Stigmas: Color — 150D.

Hips: None observed.

PLANT

Form: Compact, upright, growing close to the ground.

Growth: Vigorous, relatively little branching, attains height of 12 to 15 inches.

Foliage: Compound 3 to 5 leaflets.

*Size.*—Medium large for miniature.

*Quantity.*—Adequate.

*Color.*—New foliage: Upper side — near to 137A. Under side — near to and 138C. Old foliage: oval, pointed. Upper side — 137C. Under side — 148C.

*Shape.*—Oval, pointed.

*Texture.*—Matt on upper side; matt and marked veining on under side.

*Edge.*—Finely serrated.

*Serration.*—Fine pointed — well defined.

*Leaf stem.*—Color — near to 178A. Under side — 143C.

*Stipules.*—Medium length, long, pointed.

*Resistance to disease.*—Blackspot — good. Mildew — good.

Wood:

*New wood.*—Color — near 138B. Bark — smooth.

*Old wood.*—Color — 139B to 139C. Bark — smooth.

Thorns:

*Thorns.*—Quantity: very few. On laterals — few to none. Form — Small, pointed. Length — Small. Color — when young — 45D; when mature — 26C. Position — Irregular at branch junctions.

*Prickles.*—None.

*Winter Hardiness.*—Good winter hardiness, needs some winter protection in extreme climate.

I claim:

1. A new and distinct variety of rose plant of the miniature class, substantially as shown and described, characterized particularly by high centered, recurrent flowers of attractive coloring borne primarily singly on long stems and having a spiral, circular outline with outer petals which lighten and inner petals which deepen in color on aging so as to produce a two-tone effect and a light lavender pink tonality and a vigorous, upright growing plant.

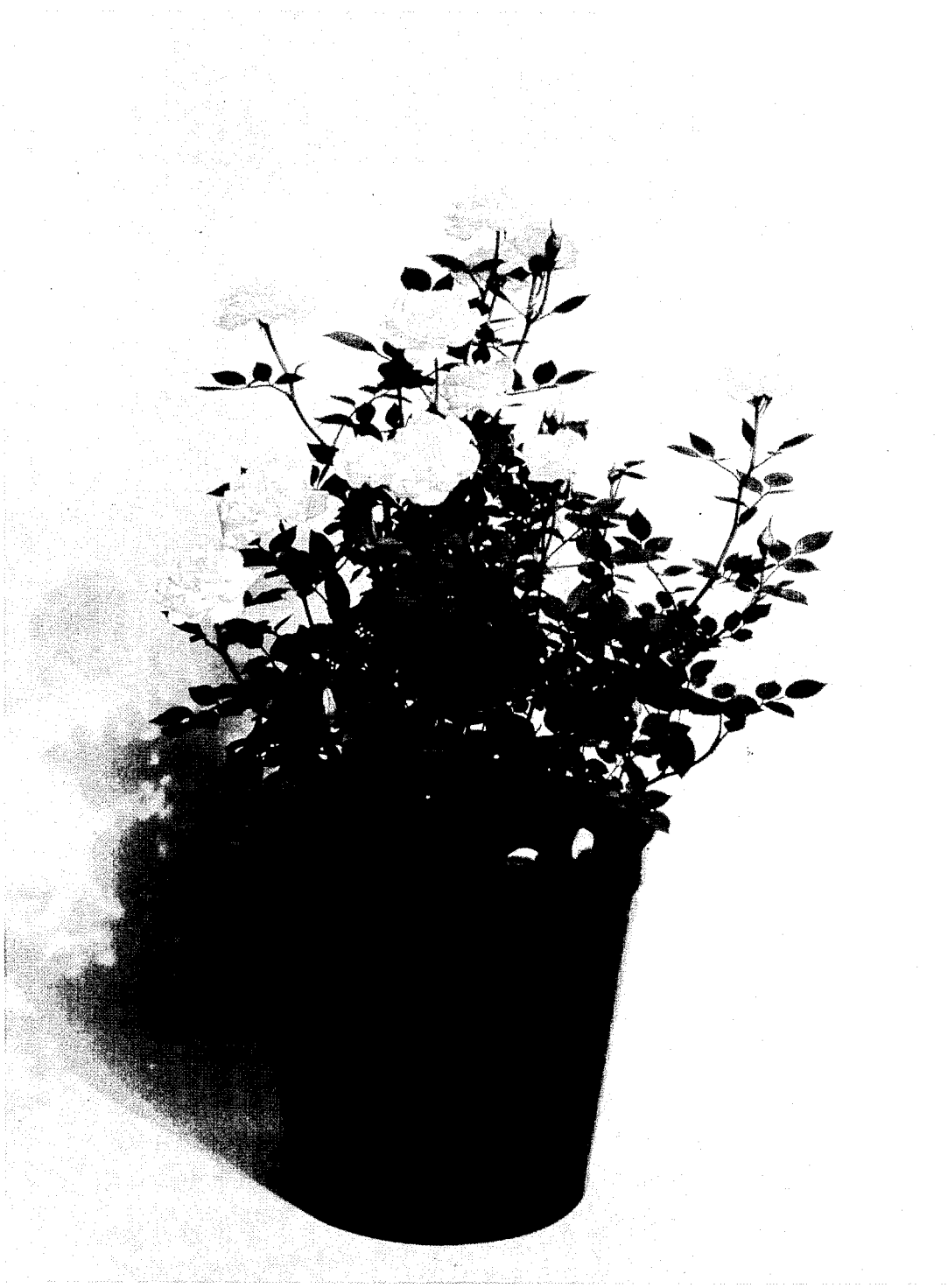

* * * * *